(12) United States Patent
Lineaweaver (10) Patent No.: US 8,401,978 B2
(45) Date of Patent: Mar. 19, 2013

(54) USING A GENETIC ALGORITHM EMPLOYING AN EXPEDITED CONVERGENCE MECHANISM TO AT LEAST PARTIALLY FIT A MEDICAL IMPLANT TO A PATIENT USING PATIENT FEEDBACK

(75) Inventor: Sean Lineaweaver, Parker, CO (US)

(73) Assignee: Cochlear Limited, Macquarie University, NSW (AU)

( * ) Notice: Subject to any disclaimer, the term of this patent is extended or adjusted under 35 U.S.C. 154(b) by 666 days.

(21) Appl. No.: 12/557,233

(22) Filed: Sep. 10, 2009

(65) Prior Publication Data

US 2011/0060702 A1    Mar. 10, 2011

(51) Int. Cl.
*G06F 15/18* (2006.01)

(52) U.S. Cl. ............................................. 706/12; 607/57

(58) Field of Classification Search ................. 706/12–1, 706/45, 623; 607/55–57
See application file for complete search history.

(56) References Cited

U.S. PATENT DOCUMENTS

| | | | |
|---|---|---|---|
| 4,532,930 A | 8/1985 | Crosby et al. | |
| 4,953,112 A | 8/1990 | Widin et al. | |
| 5,095,904 A | 3/1992 | Seligman et al. | |
| 5,277,694 A | 1/1994 | Leysieffer et al. | |
| 5,626,629 A | 5/1997 | Faltys et al. | |
| 6,157,861 A | 12/2000 | Faltys et al. | |
| 6,272,479 B1 * | 8/2001 | Farry et al. ...................... | 706/13 |
| 6,697,674 B2 | 2/2004 | Leysieffer | |
| 7,343,021 B2 | 3/2008 | Takagi et al. | |
| 2002/0176584 A1 | 11/2002 | Kates | |
| 2003/0133578 A1 | 7/2003 | Durant | |
| 2005/0107845 A1 | 5/2005 | Wakefield et al. | |
| 2005/0129262 A1 | 6/2005 | Dillon et al. | |
| 2008/0165978 A1 | 7/2008 | Cronin et al. | |
| 2010/0152813 A1 | 6/2010 | Lineaweaver et al. | |
| 2010/0280307 A1 * | 11/2010 | Lineaweaver et al. .......... | 600/25 |
| 2011/0060383 A1 | 3/2011 | Lineaweaver et al. | |
| 2011/0060384 A1 * | 3/2011 | Lineaweaver .................. | 607/57 |
| 2012/0116480 A1 * | 5/2012 | Tsay et al. ...................... | 607/57 |

FOREIGN PATENT DOCUMENTS

| | | |
|---|---|---|
| JP | 09-325773 | 12/1997 |
| JP | 11-513539 | 11/1999 |
| JP | 2003-6171 | 1/2003 |
| WO | WO 2007/090243 | 8/2007 |

OTHER PUBLICATIONS

Trautmann, et al., A Convergence Criterion for Multiobjective Evolutionary Algorithms Based on Systemic Statistical Tsting, 2008, Springer-Verlag, pp. 825-836.*
Rudolph, Convergence Analysis of Conical Genetic Algorithms, 1994, IEEE, pp. 96-101.*

(Continued)

*Primary Examiner* — David Vincent
(74) *Attorney, Agent, or Firm* — Kilpatrick, Townsend & Stockton, LLP.

(57) ABSTRACT

Apparatus and method for at least partially fitting a medical implant system to a patient is described. These apparatuses and methods comprise executing a genetic algorithm to select a set of parameter values for the medical implant system. This genetic algorithm may comprise generating successive generations of child populations until a confidence threshold is reached. This confidence threshold comprises determining whether the values of each parameter value to be selected have converged on particular value with a specified confidence level. In determining whether the values have converged, one or more initial generations of the search may be excluded in computing the likelihood that the value has converged.

24 Claims, 7 Drawing Sheets

OTHER PUBLICATIONS

Hideyuki Takagi, IEC-based Hearing Aid Fitting, IEEE SM C' 99 Conference Proceedings, Oct. 1999, vol. 3, 657-662 (6 pages).

International Search Report for International Application No. PCT/IB2010/054105 mailed Jun. 14, 2011 (5 pages).

European Official Communication for European Application No. 04 719 779.3 mailed Apr. 20, 2011 (3 pages).

Canadian Intellectual Property Office, "Office Action," issued in connection with Canadian Patent Application Serial No. 2,518,997, on Apr. 16, 2010 (2 pages).

Skinner, et al., "Speech Recognition with the Nucleus 24 SPEAK, ACE, and CIS Speech Coding Strategies in newly Implanted Adults," Ear & Hearing, vol. 23, No. 3, 208-223, (Jun. 2002) (17 pages).

Skinner, et al., "Nucleus 24 Advanced Encoder Conversion Study: Performance versus Preference," Ear & Hearing, vol. 23, No. 18, 3S-7S, (Feb. 2002) (16 pages).

Wakefield, et al., "Recipient-Directed Design of Speech processor MAPs," in R.T. Miyamoto, ed., Cochlear Implants, Elsevier, International Congress Series, 1273 148-182 (2004) (5 pages).

Wakefield, et al., "Genetic Algorithms for Adaptive Psychopysical Procedures: Recipient-Directed Design of Speech-Processor MAPs," Ear & Hearing, 52S-72S, (Aug. 2005) (16 pages).

Japanese Office Action for Japanese Application No. 2006-507068 mailed on Jun. 1, 2010 along with English translation (4 pages).

Japanese Office Action for Japanese Application No. 2006-507068 mailed on Mar. 8, 2011 along with English translation (3 pages).

Japanese Office Action for Japanese Application No. 2006-507068 mailed on Oct. 18, 2011 along with English translation (5 pages).

International Search Report for PCT/US04/07400 mailed Aug. 27, 2004.

Written Opinion for PCT/US04/07400 dated Aug. 27, 2004.

Forrest, Stephanie, "Genetic Algorithms: Principles of Natural Selection Applied to Computation," Science, Aug. 13, 1993, vol. 261 (5123), pp. 872-878.

Takagi, Hideyuki, "Interactive Evolutionary Computation: Fusion of the Capabilities of EC Optimization and Human Evaluation," Proceedings of the IEEE, Sep. 2001, vol. 89, No. 9, pp. 1275-1296.

* cited by examiner

USING A GENETIC ALGORITHM EMPLOYING AN EXPEDITED CONVERGENCE MECHANISM TO AT LEAST PARTIALLY FIT A MEDICAL IMPLANT TO A PATIENT USING PATIENT FEEDBACK

CROSS-REFERENCE TO RELATED APPLICATIONS

This application is related to PCT Application No. PCT/US2004/007400, U.S. Pat. Nos. 4,532,930, 5,277,694, 6,123,660, 6,162,169, 6,537,200, 6,565,503, 6,575,894, 6,697,674, 6,879,860, U.S. patent application Ser. No. 10/963,594, entitled "Using a Genetic Algorithm to Fit a Cochlear implant System to a Patient," filed Oct. 13, 2004, U.S. patent application Ser. No. 12/577,208, entitled "Using a Genetic Algorithm to Fit a Medical Implant System to a Patient," filed concurrent with the present application, and U.S. patent application Ser. No. 12/557,218, entitled "Using a Genetic Algorithm Employing Dynamic Mutation," filed concurrent with the present application. The entire disclosure and contents of the above patents are hereby incorporated by reference herein.

BACKGROUND

1. Field of the Invention

The present invention relates generally to stimulating medical devices, and more particularly, to fitting a stimulating medical device.

2. Related Art

Many medical devices have structural and/or functional features which are to be adjusted for an individual patient. The process by which a medical device is tailored or customized for the specific needs of a patient is commonly referred to as fitting. One type of medical device which is typically fitted to individual recipients is a cochlear implant system.

Cochlear implant systems provide the benefit of hearing to individuals suffering from severe to profound hearing loss. Hearing loss in such individuals is often due to the absence or destruction of the hair cells in the cochlea which transduce acoustic signals into nerve impulses. Cochlear implant systems essentially stimulate the auditory nerves by directly delivering electrical stimulation to the auditory nerve fibers. This causes the brain to perceive a hearing sensation resembling the natural hearing sensation normally delivered by the auditory nerve. Examples of cochlear implant systems are described, by way of example, in U.S. Pat. Nos. 4,532,930, 6,537,200, 6,565,503, 6,575,894, and 6,697,674, among others.

Conventional cochlear implant systems commonly include an external assembly directly or indirectly attached to the body of the patient (sometimes referred to herein as the recipient), and an internal assembly which is implanted in the patient. The external assembly typically comprises one or more microphones for detecting sound, a speech processing unit that converts detected sound into an electrical coded signal, a power source, and an external transcutaneous transfer coil. The internal assembly typically comprises an internal transcutaneous transfer coil, a stimulator unit located within a recess of the temporal bone of the recipient, and an electrode array positioned in the recipient's cochlea. Completely implantable cochlear implant systems having functionally similar components are under development.

In addition to providing electrical stimulation, some cochlear implant systems also include a mechanical stimulation mode of operation. Such so called mixed-mode systems offer rehabilitation by mechanically stimulating a portion of a patient's auditory pathway, either acoustically or physically. For example, there have been approaches to offer rehabilitation with conventional hearing aids via the application of an amplified acoustic signal to the external auditory canal, or by physically stimulating an ossicle of the middle ear or the inner ear via mechanical or hydromechanical stimulation.

Modern cochlear implant systems provide a wide variety of fitting options that can be customized for an individual patient. Because patients are heterogeneous, each patient requires a different set of parameters to maximize speech reception and patient satisfaction. The task of the clinical professional, usually an audiologist, is to select a set of parameters, commonly referred to as a parameter map or, more simply, a MAP, that will provide the best possible sound reception for an individual patient. Because there may be thousands of possible parameter maps, it is impractical for a patient to experience all of the alternatives and to evaluate the performance of each alternative. Nor is it possible to identify an optimal parameter map by prescription based on a limited set of measurements as is, for example, the case in fitting eyeglasses. Because parameters of cochlear implant systems often interact non-linearly and non-monotonically, it is also not possible to sequentially optimize parameters one at a time, adjusting each in succession to its optimal value.

As a result, clinicians have adopted a variety of approaches for fitting the cochlear implant systems to a patient. Some simply set the parameters to default values regardless of the individual patients. Others adopt preferred parameter maps, which they believe are good, if not best, for many or most patients. The preferences may be based on personal experience, published performance data, or intuition. Some clinicians evaluate a limited set of alternatives adjusting individual parameters based upon measured perceptual limitations and inferred relationships among the parameters. These approaches are time consuming, costly, and unreliable, and typically fail to achieve the optimal outcome for individual patients.

SUMMARY

In one aspect of the present invention there is provided a method for at least partially fitting a medical implant system to a patient comprising: executing a genetic algorithm to select a determined value set comprising values for a plurality of fitting parameters, the genetic algorithm comprising: presenting signals processed by a plurality of value sets to the patient using the medical implant system; receiving patient feedback in response to the presented signals processed by the value sets; selecting, based on the patient feedback, one or more of the value sets; computing a likelihood of convergence for at least one value of the value set using values from a plurality of previously generated generations and not using values from one or more of the previously generated generations; generating a successive generation of value sets using said selected one or more value sets; and repeating the steps of presenting, receiving, selecting, and generating until the computed likelihood of convergence exceeds a confidence level; and providing said determined value set to said medical implant system for use in providing stimulation to the patient.

In another aspect of the present invention, there is provided a system for at least partially fitting a medical implant system to a patient comprising: a processor configured to execute a genetic algorithm to select a determined value set comprising values for a plurality of fitting parameters, wherein the processor in executing the genetic algorithm is configured to present a plurality of value sets to the patient using the medical implant system, receive patient feedback in response to the presented signals processed by the value sets, select, based on the patient feedback, one or more of the value sets, compute a likelihood of convergence for at least one value of the value set using values from a plurality of previously generated generations and not using values from one or more of the previously generated generations, generate a successive generation of value sets using said selected one or more value sets; and repeat the steps of presenting, receiving, selecting, and generating until the computed likelihood of convergence exceeds a confidence level; and an interface configured to provide at least one of the value sets to the medical implant system for use by the medical implant system in providing stimulation to the patient.

In yet another aspect of the present invention, there is provided a system for at least partially fitting a medical implant system to a patient comprising: means for executing a genetic algorithm to select a determined value set comprising values for a plurality of fitting parameters, the genetic algorithm comprising: means for presenting signals processed by a plurality of value sets to the patient using the medical implant system; means for receiving patient feedback in response to the presented signals processed by the value sets; means for selecting, based on the patient feedback, one or more of the value sets; means for computing a likelihood of convergence for at least one value of the value set using values from a plurality of previously generated generations and not using values from one or more of the previously generated generations; means for generating a successive generation of value sets using said selected one or more value sets; and means for repeating the steps of presenting, receiving, selecting, and generating until the computed likelihood of convergence exceeds a confidence level; and means for providing said determined value set to said medical implant system for use in providing stimulation to the patient.

In yet another aspect there is provided a computer-readable media encoded with instructions operative to cause a computer to perform a method for at least partially fitting a medical implant system to a patient, the method comprising: executing a genetic algorithm to select a determined value set comprising values for a plurality of fitting parameters, the genetic algorithm comprising: presenting signals processed by a plurality of value sets to the patient using the medical implant system; receiving patient feedback in response to the presented signals processed by the value sets; selecting, based on the patient feedback, one or more of the value sets; computing a likelihood of convergence for at least one value of the value set using values from a plurality of previously generated generations and not using values from one or more of the previously generated generations; generating a successive generation of value sets using said selected one or more value sets; and repeating the steps of presenting, receiving, selecting, and generating until the computed likelihood of convergence exceeds a confidence level; and providing said determined value set to said medical implant system for use in providing stimulation to the patient.

BRIEF DESCRIPTION OF THE DRAWINGS

Embodiments of the present invention are described below with reference to the attached drawings, in which.

DETAILED DESCRIPTION

Aspects of the present invention are generally directed to the use of a genetic algorithm in fitting a stimulating medical device. In certain embodiments, the fitting system uses an expedited convergence strategy that terminates the genetic algorithm search when the genetic algorithm is determined to have converged on a particular solution. Convergence on a particular solution may be determined by analyzing the statistical history of all previously selected possible solutions, and determining that the solutions have converged when each value of the solutions can be estimated with a specified confidence. In some embodiments, the possible solutions are MAPs specifying parameter values for a subset of parameters of the stimulating medical device.

Early generations of a genetic algorithm search are often deliberately random, and thus if included in a convergence calculation, may delay the determination that the genetic algorithm search has converged. In an embodiment, these early generations may be excluded in the determination of whether the genetic algorithm has converged on a particular solution. However, the exact number of early generations that should be excluded may vary among genetic algorithm searches. In an embodiment, every possible number of excluded early generations may be analyzed in determining whether the genetic algorithm search has converged on a particular solution. Then, the genetic algorithm search may be determined when any of the possible exclusions of early generations provides a determination that the genetic algorithm search has converged. An exemplary embodiment of a genetic algorithm using an expedited convergence calculation will be discussed in more detail below after a presentation of an exemplary environment for implementation of such an algorithm.

Figure 1:
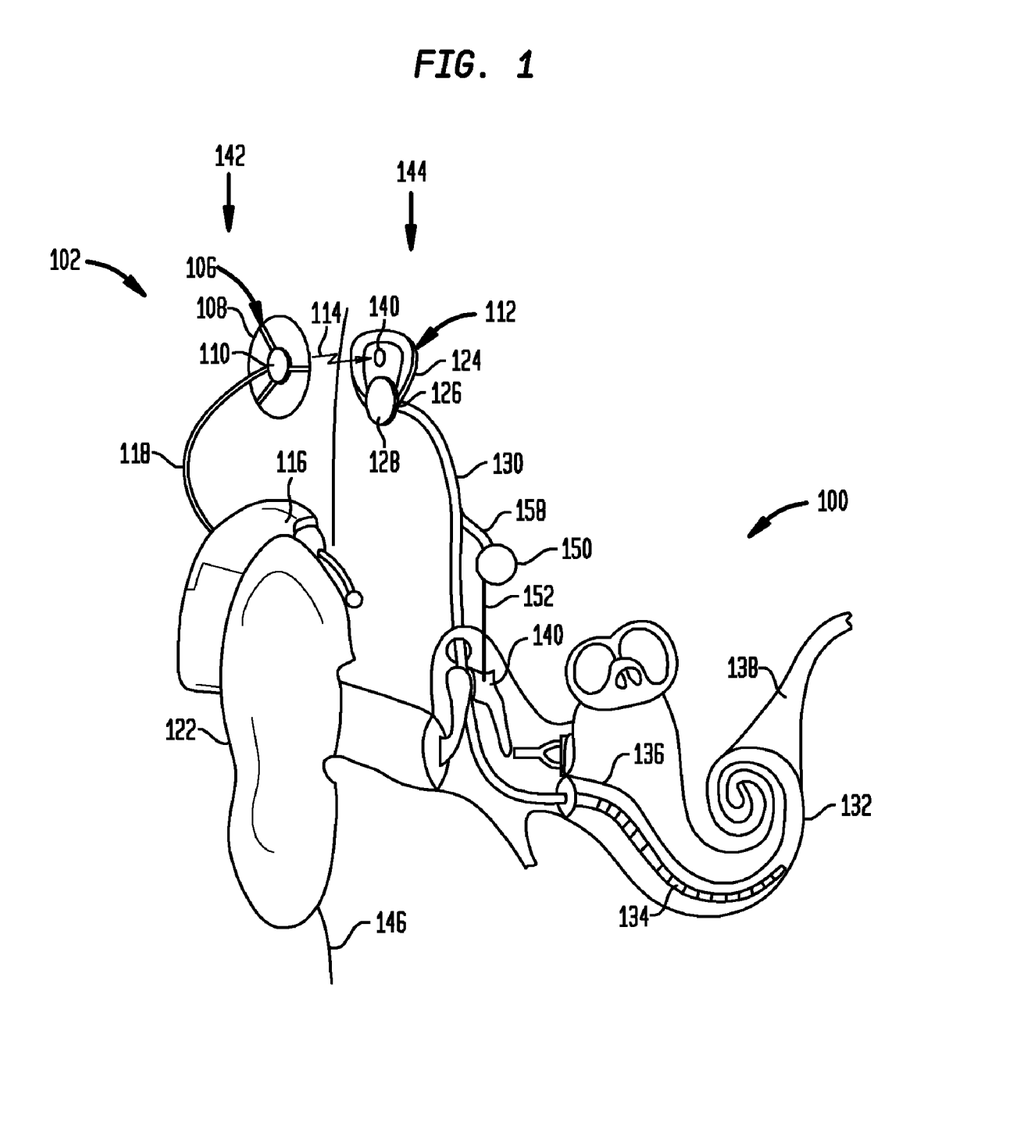
FIG. 1 is a schematic diagram of an exemplary cochlear implant system which may be fitted to an individual patient in accordance with an embodiment.

FIG. 1 is a schematic diagram of an exemplary cochlear implant system 100 which may be fitted to an individual patient in accordance with embodiments of the present invention. This embodiment of cochlear implant system 100 has single- and mixed-mode operational capabilities. With regard to an electrical stimulation mode of operation, cochlear implant system 100 provides direct electrical stimulation of auditory nerve cells to bypass absent or defective hair cells that normally transduce acoustic vibrations into neural activity. In this illustrative embodiment, cochlear implant system 100 comprises external component assembly 142 which is directly or indirectly attached to the body of the patient, and an internal component assembly 144 which is temporarily or permanently implanted in a patient. External assembly 142 typically comprises at least one audio pickup device such as a microphone (not shown) for detecting sounds, a speech processing unit 116 that converts the detected sounds into a coded signal, a power source (not shown), and an external transmitter unit 106. External transmitter unit 106 comprises an external coil 108, and, preferably, a magnet 110 secured directly or indirectly to external coil 108. Speech processor 116 processes the output of the audio pickup devices that may be positioned, for example, by the ear 122 of the recipient. Speech processor 116 generates stimulation signals which are provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to basilar membrane 136 thereby stimulating auditory nerve 138. Typically, the electrodes differentially activate auditory neurons that normally encode differential pitches of sound.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone molding (not shown). In use, implantable receiver unit 112 may be positioned, for example, in a recess of the temporal bone adjacent ear 122 of the recipient.

Regarding the mechanical mode of operation, cochlear implant system 100 provides, in this illustrative embodiment, direct mechanical stimulation to the patient's middle ear.

Electromechanical transducer 150 is coupled to the middle ear or inner ear using any technique now or later developed. Transducer 150 stimulates the impaired inner ear by direct mechanical coupling via coupling element 152 to a middle ear ossicle or via an air gap coupling for implantable transducers which are electromagnetic, for example. In this illustrative embodiment, electromechanical transducer 150 is coupled to incus 140. One example of transducer 150 is described in U.S. Pat. No. 5,277,694 which is hereby incorporated by reference herein. In the embodiment of a hermetically tight transducer described therein, a housing wall of the transducer is designed as a vibrating membrane which, together with a piezoelectric ceramic wafer applied to the inside thereof, comprises an electromechanically active composite element, the mechanical vibrations of which are transmitted to the ossicular chain via a coupling rod 152 permanently attached to the outside of the membrane. Optionally, coupling rod 152 can be attached to the membrane via a coupling element which is connected to the coupling rod. Alternatively, transducer 150 can be implemented as described in U.S. Pat. No. 6,123,660 which is hereby incorporated by reference. In such an embodiment, a permanent magnet is attached to the inside of the piezoelectric ceramic wafer to interact with an electromagnetic coil, such as an electromagnetic transducer. Such a combined piezoelectric-electromagnetic transducer is advantageous in particular with respect to a wide frequency band and achieving relatively high vibration amplitudes with comparatively small supplied energy.

In an alternative embodiment, transducer 150 can be an electromagnetic transducer arrangement as is described in commonly owned U.S. Pat. No. 6,162,169 which is hereby incorporated by reference herein. In such an embodiment, the transducer arrangement comprises a housing which can be fixed at the implantation site with reference to the skull, with a mechanically stiff coupling element which can move relative to the housing. In the housing there is an electromechanical transducer which to vibrates the coupling element.

The above signal processing components are controlled by a microcontroller included, for example, in speech processor 116. The microcontroller includes a storage area in which patient-specific audiologic adaptation parameters and the audiometry parameters of the above-noted signal generator are stored. The microcontroller and associated data storage may be implantable, such as within stimulator unit 126. In such embodiments, the programmable data are sent to the microcontroller via telemetry unit 102.

As noted, there may be a substantial number of parameters which may be customized to optimally fit a cochlear implant system to an individual patient. As will be described below, not all parameters may be selected to obtain values with the genetic algorithm. The selected subset of parameters and their respective values is collectively and generally referred to herein as a "parameter map," a "cochlear map" or "MAP." A "MAP" is also sometimes referred to as a "program."

Examples of parameters include, for example, the speech strategy implemented in the cochlear implant system. Additionally, within any given speech strategy a great many parameters may be specified to tailor the encoding and stimulation for an individual patient. Examples of parameters and parameter values that may be selected for a speech strategy include but are not limited to the number of channels of stimulation represented, the configuration and number of intracochlear and/or extracochlear electrodes which are to be associated with each channel, the pulse repetition rate for each channel, the pulse pattern, the width of each pulse or between pulses, the number of spectral maxima periodically chosen for representation, the mapping of sound pressure to stimulus current for each channel (threshold levels, comfort levels and compression curves), the frequency boundaries allocated for each channel, parameters for the front end filtering of the audio from the microphone (pre-emphasis), and automatic gain control threshold, channel-specific compression ratios, and attack and release times.

In cochlear implant systems such as system 100 described above which provide electrical and mechanical stimulation, additional parameters may be selected to tailor the cochlear implant system to an individual patient. Such parameters include, but are not limited to, loudness parameters such as long term loudness balance (that is, electrical and mechanical gains), parameters for short term gain manipulations, particularly signal-dependent gain adjustments. Such gain adjustments parameters include, for example, parameters for adjustments to minimize cross-modal masking, and adjustments to emphasize speech features such as noise, friction or voicing.

Additional parameters may include frequency domain parameters. Such parameters include, for example, overall frequency boundaries allocated to electrical and mechanical stimulation, slopes of filtering at the boundaries of each stimulation signal, allocation of frequency subbands (both quantity and boundaries) in each domain, etc. Also, filtering of the mechanical signal within the passband, for example, to match the hearing loss or for other purposes.

Additional parameters may also include time domain parameters. Such parameters include, for example, parameters for adjusting electrical periodicity of pulse timing to be synchronized with the mechanical signal fluctuations, adjusting delays in the electrical stimulus to compensate for missing propagation delays of various middle ear and inner ear pathways, etc.

Additional parameters may also include binaural parameters. Such parameters include, for example, parameters for adjusting stimulus timing to preserve interaural timing cures, adjustment of stimulus timing to suppress echo, improve localization, or improve sound source segregation, etc.

As used herein, the term 'parameter values' generally and collectively refers to values of parameters, whether selectable options are programmed on or off, and in general to any choices that are made during a fitting procedure. As one or ordinary skill in the art would appreciate, the above parameters are an example of mixed-mode parameters which may be selected and tailored to optimally fit a single-mode (electrical stimulation) and for mixed-mode (electrical and mechanical stimulation) cochlear implant system to a patient.

Figure 2:
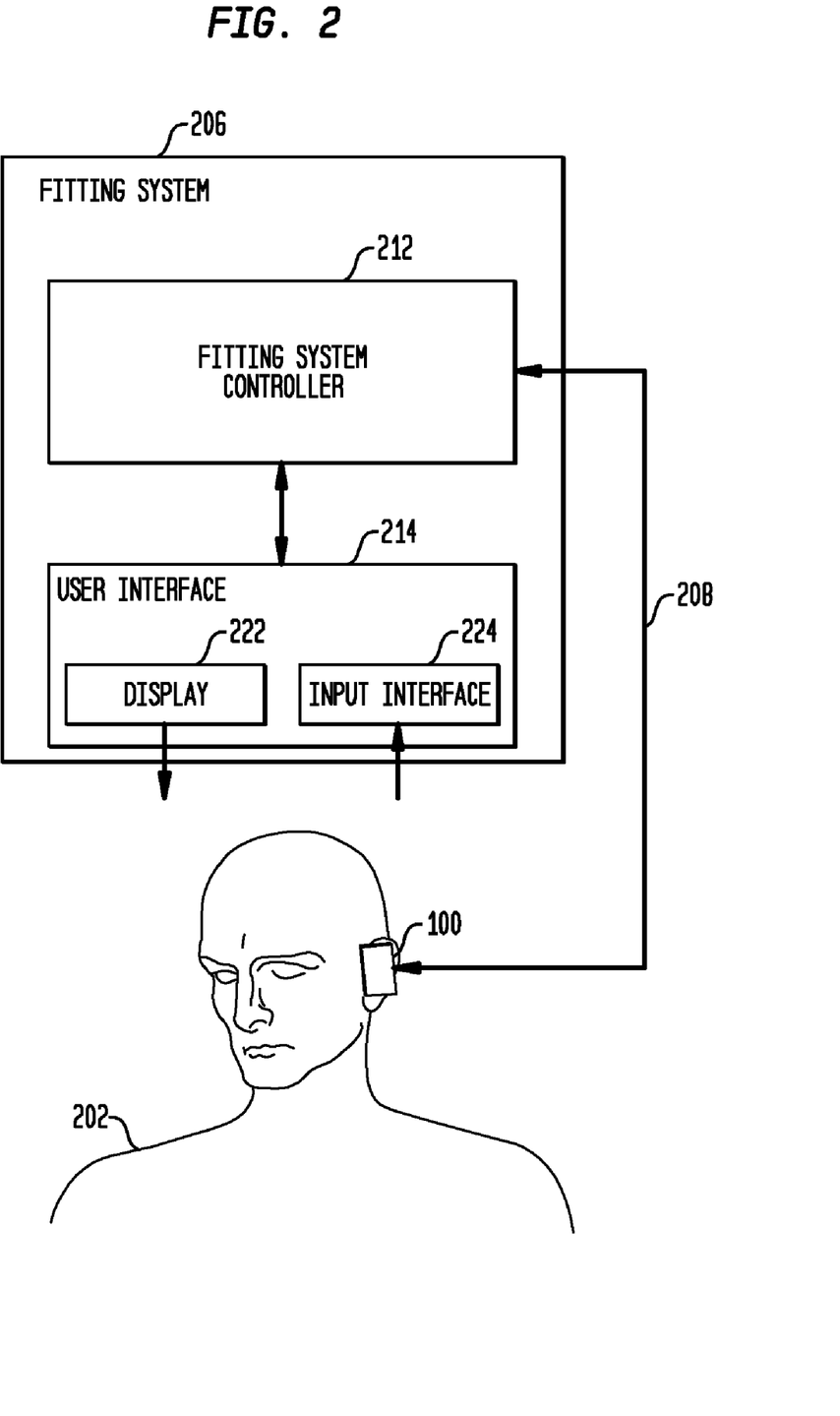
FIG. 2 is a schematic diagram illustrating one exemplary arrangement in which a recipient operated fitting system may be used in fitting a stimulating medical device, in accordance with an embodiment.

FIG. 2 is a schematic diagram illustrating one exemplary arrangement 200 in which a patient 202 operated fitting system 206 may be used in fitting a stimulating medical device, such as a cochlear implant 100, in accordance with an embodiment. In the embodiment illustrated in FIG. 2, sound processing unit 126 of cochlear implant 100 may be connected directly to fitting system 206 to establish a data communication link 208 between the sound processing unit 126 and fitting system 206. Fitting system 206 is thereafter bi-directionally coupled by means of data communication link 208 with sound processing unit 126. It should be appreciated that although sound processing unit 126 and fitting system 206 are connected via a cable in FIG. 2, any communications link now or later developed may be utilized to communicably couple the implant and fitting system.

Fitting system 206 may comprise a fitting system controller 212 as well as a user interface 214. Controller 212 may be any type of device capable of executing instructions such as, for example, a general or special purpose computer, digital electronic circuitry, integrated circuitry, specially designed ASICs (application specific integrated circuits), firmware, software, and/or combinations thereof. User interface 214 may comprise a display 222 and an input interface 224. Display 222 may be, for example, any type of display device, such as, for example, those commonly used with computer systems. Input interface 224 may be any type of interface capable of receiving information from a patient 202, such as, for example, a computer keyboard, mouse, voice-responsive software, touch-screen (e.g., integrated with display 222), retinal control, joystick, and any other data entry or data presentation formats now or later developed.

Figure 3:
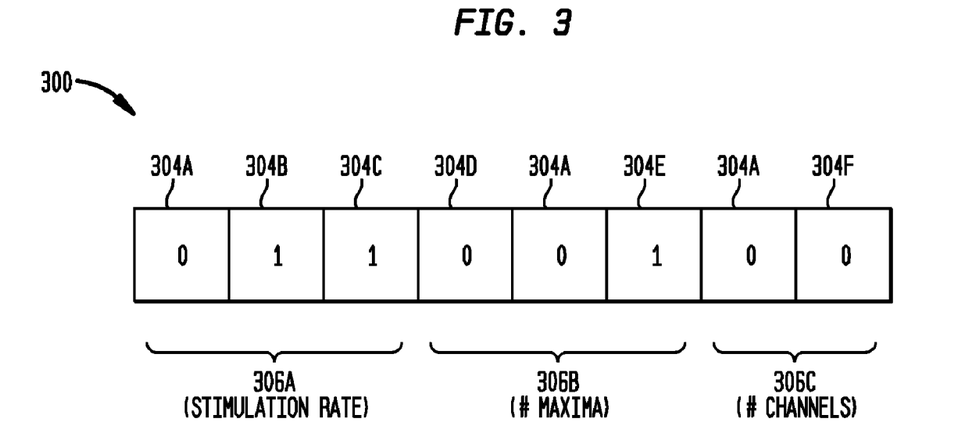
FIG. 3 illustrates an exemplary MAP comprising a set of 8 binary genes, in accordance with an embodiment.

Fitting system 206 may be configured to perform a MAP search using a genetic algorithm. In performing the genetic algorithm search, fitting system 206 may represent the MAPs using a bit string comprising a set of $N_b$ 'genes' (bits), wherein the number of possible unique MAPs is $2^{Nb}$. FIG. 3 illustrates an exemplary MAP 300 comprising a set of 8 binary genes 304A-304H ($N_b$=8). Each of the 8 bits 304 may be used to individually or collectively designate several parameters for cochlear implant system 100.

In the example shown in FIG. 3, three such parameters 306A-306C are designated. Three bits 304A-304C are used to select a parameter 306A of stimulus rate (the rate, in Hz, at which high-energy channels are selected and stimulus pulses are delivered to groups of N electrodes), three bits 304D-304F are used to select a parameter 306B of spectral maxima counts (the number N of electrodes periodically selected to be stimulated, representing the N frequency bands with the highest energy at the time), and the remaining two bits 304G-304H select a parameter 306C of the quantity of channels or frequency bands, used to represent the sound spectrum. Other parameters are assumed to be constant or derived from one of the three represented parameters 306.

It should be understood that FIG. 3 is exemplary only and provided to illustrate how a bit string may be used to represent various parameters of a MAP; and, in other embodiments the number of bits and what they represent may be different in alternative embodiments. A further description of an exemplary mechanisms for representing MAPs using bits strings is provided in U.S. patent application Ser. No. 10/963,594 entitled "Using a Genetic Algorithm to Fit a Cochlear Implant System to a Patient," the entire contents of which are hereby incorporated by reference.

Figure 4:
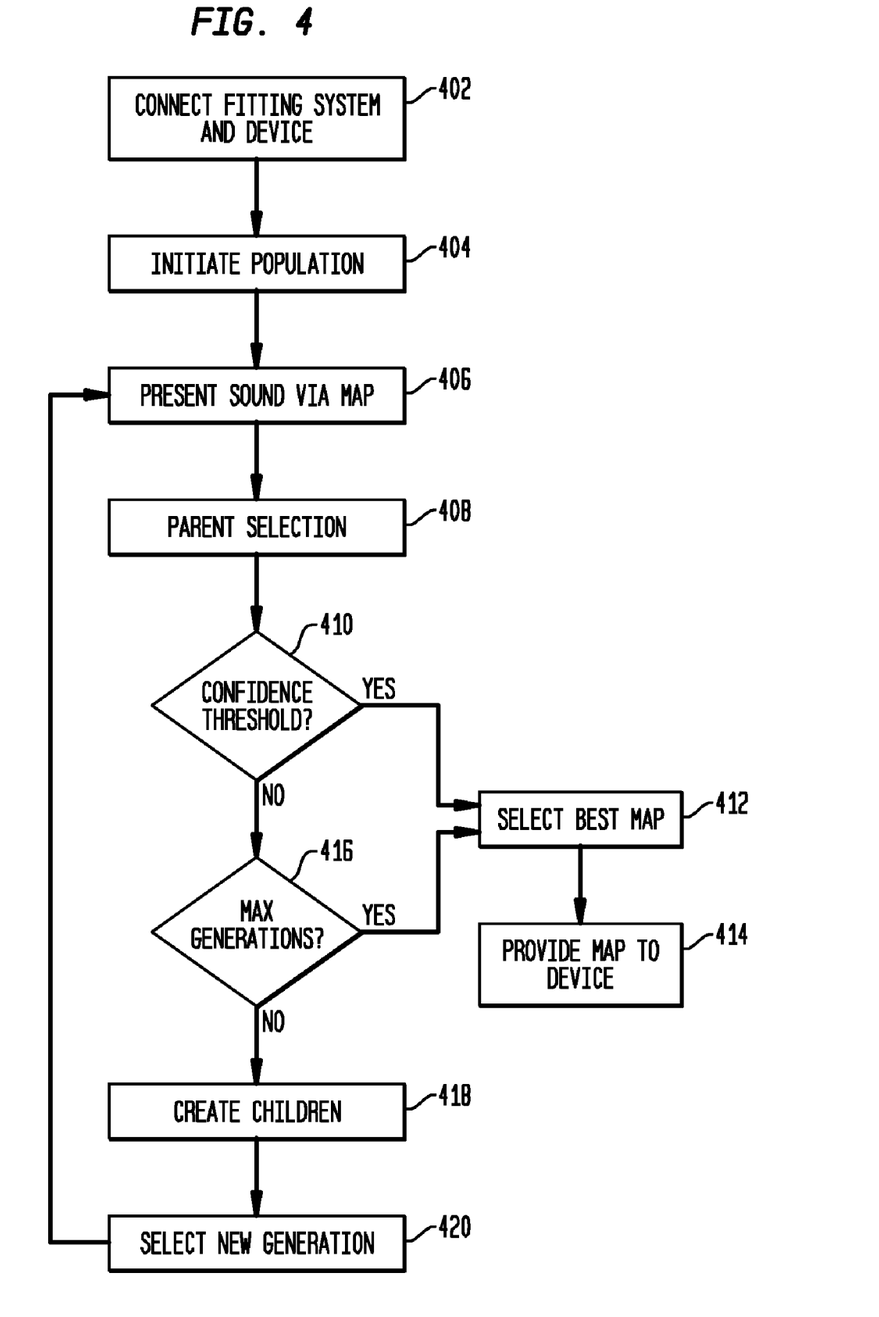
FIG. 4 is a high-level flow chart of an exemplary method for determining a MAP using a genetic algorithm, in accordance with an embodiment.

FIG. 4 is a high-level flow chart of an exemplary method for determining a MAP using a genetic algorithm, in accordance with an embodiment. FIG. 4 will be discussed with reference to the fitting system illustrated in FIG. 2.

A patient 202 may initiate the process by connecting cochlear implant 100 to fitting system 206 at block 402. This may be accomplished by plugging a cable into the speech processor 126 of the cochlear implant 100 and the fitting system 206. Or, for example, fitting system 206 and cochlear implant 100 may connect wirelessly in response to, for example, the patient 202 entering an instruction via user interface 214 that instructs fitting system 206 to wirelessly initiate a connection with cochlear implant 100. This connection may also cause the fitting system to begin some initialization procedures. These initialization procedures may include a calibration step to help ensure that if the fitting system 206 delivers a sound signal to the patient 202 via a speaker at a specified loudness, the sound may be delivered with a constant sound level pressure to the sound processing unit 126 of the cochlear implant 100 by the fitting system 206.

The fitting system 206 may generate an initial population of MAPs at block 404. In an embodiment, the initial population may comprise 8 selected MAPs. It should be noted that this number need not be 8, but may vary depending on the implementation. Various techniques may be used to select this initial generation of MAPs. For example, this selection may be performed by selecting at random from among the set of possible MAPs. Or, for example, in order to insure greater diversity among the selected initial generation of MAPs, the MAPs may be selected so that the each parameter value is represented in at least one MAP. For parameters in which the number of possible variables is greater than the number of MAPs in the initial generation, the values may be randomly selected such that each MAP in the initial generation has a unique value for the parameter. For example, if there are 12 possible parameter values, a first one of the parameter values may be randomly selected from among the 12 possible values, and then when selecting the parameter value for the second MAP the fitting system selects from amongst the 11 remaining unselected values, and so on.

Or, for example, in an embodiment, in order to insure that this initial MAP set has a sufficient measure of heterogeneity, its diversity may computed. In one embodiment, diversity is defined as the average Hamming distance between the various MAPs, and it ranges between 0 and 1, with 1 indicating maximum diversity and 0 indicating minimum diversity. If the diversity is below a threshold, for example, 0.53, then the initial generation has an insufficient diversity, and the fitting system 206 may select a new set of MAPs. Moreover, preselected MAPs may also be included among the MAPs of the first generation. These pre-selected MAPs may be drawn, for example, from prior runs of the fitting procedure, MAPs stored in a memory of fitting system 206, or MAPs selected by a clinician based on his experience, suggestions and recommendations from others, etc. This initial population of MAPs may be referred to as the first generation of MAPs.

At block 406, audible signals processed by the population of MAPs are presented to the patient. This may involve fitting system 206 sequentially providing each MAP to the patient's cochlear implant 100 and then presenting an audible signal that that is processed by the provided MAP. The audible signal may be a sound token that comprises any type of sound, such as a single speaker reading aloud from a newspaper or a passage from an audio book, a particular piece of music, or portion of same, a musical instrument, a car horn, etc. The audible signals (e.g., sound tokens) may be stored in a file contained in a library of audible signals that is stored, for example, in fitting system 206 or in an external storage device connected to fitting system 206.

In an embodiment, fitting system 206 may randomly select a sound token for each of the 8 MAPs. Fitting system 206 may then download the MAP corresponding to a particular sound token to the cochlear implant, and then play the audible signal (e.g., the sound token). This audible signal may be played using, for example, one or more speakers connected to fitting system 206, such as, for example, a set of headphones worn by the patient 202. Further, patient 202 and fitting system 202 may be located in a room such as, for example, a sound proof room, designed to minimize external noise interfering with the presentation of the audible signal. Or, for example, fitting system 206 may provide the audible signal directly to cochlear implant 100 via data communications link 208. After fitting system 206 presents the first sound token to the patient 202, the fitting system 206 may download the next MAP to the cochlear implant 100 and then play the corresponding sound token to the patient 202. This process may then continue sequentially until fitting system 206 presents sound tokens processed by all 8 MAPs to the patient 202.

After fitting system 206 presents each of the sound tokens and corresponding MAPs to the patient 202, fitting system 206 may then receive an indication from the patient 202 regarding which sound tokens were perceived as good by the patient 202. Using this indication, fitting system 206 may determine the parents for the next generation of MAPs at block 408. In an embodiment, all MAPs identified as good by the patient 202 may be selected as parent MAPs for generating the next generation of MAPs. Or, for example, the patient 202 may select the 4 MAPs that the patient considered to be the best MAPs and these 4 best MAPs are selected as the parent MAPs.

In yet another embodiment, the patient may be presented with a sound token comprising a statement, and the patient asked to identify what they heard. Then, if the patient 202 correctly identified what they heard, the corresponding MAP may be used as a parent MAP generating the next generation of MAPs. A further description of user interface that may be used to perform such an objective test in identifying good MAPs is presented below with reference to FIG. 7.

It should be noted that these are but some exemplary mechanisms that may be used at blocks 406 and 408 for selecting parent MAPs from the population of MAPs, and other mechanisms may be used without departing from the present invention. For example, mechanisms for selecting parent MAPs may be used such as described in U.S. patent application Ser. No. 12/557,208, entitled "Using a Genetic Algorithm to Fit a Medical Implant System to a Patient," the entire contents of which are hereby incorporated by reference. Further, it should be noted that although blocks 406 and 408 are illustrated as separate blocks, this was done for illustrated purposes, and in embodiments they may be combined or involve an iterative process where the two blocks are repeated until a certain condition occurs, such as all MAPs are presented or a particular number of MAPs are selected.

Fitting system 206 may then check to see if a confidence threshold has been reached at block 410 for the selected MAPs. In an embodiment, fitting system 206 may determine that the confidence threshold has been reached if the value of each bit of the MAP bit string is considered to have converged and its value is known with a particular confidence level based on the historical distribution of that bit. For instance, bit #1 may be considered converged if it has historically either been either a "1" or a "0" a particular percentage of the time (e.g., 95% of the time according to a binomial distribution) over its entire history. As such, probability dictates that there is a 95% chance that this bit will be the same value again in a subsequent generation. When all bits reach this confidence level (e.g., 95%), fitting system 206 may determine that the confidence threshold has been met. In other words, in this example, the fitting system 206 determines that the confidence threshold has been met if the confidence level for each of the bits exceeds the specified confidence level (e.g., 95%).

An embodiment uses an expedited convergence algorithm that may analyse a multitude of historical sequences of generations from every possible initial generation through the current/latest generation. Computing confidence levels using, in an embodiment, every possible historical sequence of generations may help expedite the convergence of the algorithm. An exemplary mechanism for such an expedited convergence algorithm is discussed below with reference to FIG. 6.

If at block 410 the confidence threshold has not been achieved, fitting system 206 may determine if the maximum number of generations has been reached at block 416. If so, fitting system 206 may proceed to block 410 to select the final MAP. Otherwise the algorithm continues to block 418.

Fitting system 206 may determine if the maximum number of generations has been reached by maintaining a tally of each pass through block 416 and then comparing this tally against a particular value specifying the maximum number of generations to be used in determining the final MAP. For example, in an embodiment, fitting system 206 may set a generation number variable, G, equal to one (G=1) at block 404, and then increase G by 1 (G=G+1) at block 418 or 420. It should be noted that this is but one mechanism in which fitting system 206 may maintain a generation number variable G that is equal to the current generation number of the genetic algorithm search, and other mechanisms may be employed.

Fitting system may then generate child MAPs at block 418. Various techniques may be used for generating the child MAPs. For example, in an embodiment, a child MAP may be generated by pairing two of the parent MAPs selected at block, selecting a cut point, and then generating two children MAPs from the selected parents. In an embodiment, the genes for a child MAP to the left of the cut point may come from one parent, and the genes to the right of the cut point may come from the other parent.

Figure 5:
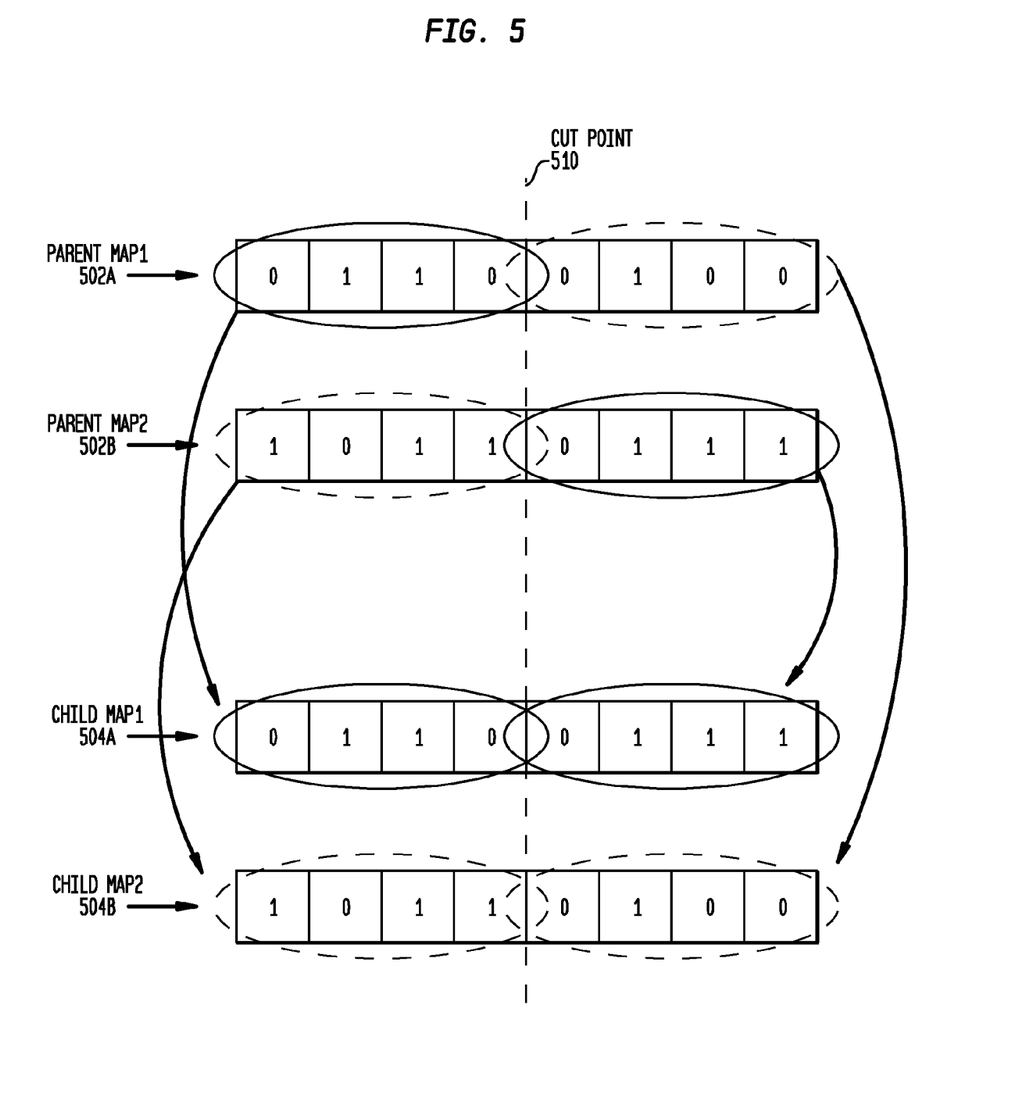
FIG. 5 illustrates one example of how an offspring MAP may inherit genes from each parent MAP, in accordance with an embodiment.

FIG. 5 illustrates one example of how an offspring MAP may inherit genes from each parent MAP, in accordance with an embodiment. In the illustrated example, each parent MAP 502A and 502B is represented by an 8 bit string. Fitting system 206 may select a cut point 510 for the bit string of each parent MAP 502A and 502B. The selected cut point 510 may be between any particular bits of the bit strings, and in FIG. 5 the cut point 510 is selected in the middle of each bit string. Further, in the illustrative example, the cut point is allowed to vary randomly across pairings. For example, in an embodiment, the fitting system 206 may analyze the two parent MAPs to identify bits that are different between the parents, and then randomly select a cut point between the bits identified to be different. Alternatively, the cut points can be made in the same position for all the pairings.

Then, fitting system 206 may generate two child MAPs 504A and 504B from the parent MAPs 502, where the first child MAP 504A includes bits of parent MAP 502A to the left of the cut point 510 (i.e., the first 4 bits) and the of the parent MAP 502B to the right of the cut point 510 (i.e., the last 4 bits). Similarly, the genes of the second child MAP 504B include the first 4 bits of parent MAP 502B and the last 4 bits of parent MAP 502A. It should be noted that this is but one example of how child MAPs may be generated from parent MAPs, and other mechanisms may be used.

Fitting system 206 may then select at block 420 the child MAPs for the next generation of MAPs to be presented to the patient (i.e., for which sound tokens are to be presented to patient 202 processed by the MAPs). Various techniques may be used for selecting the new generation of MAPs, such as those discussed in the above-referenced U.S. patent application Ser. No. 12/557,208, entitled "Using a Genetic Algorithm to Fit a Medical Implant System to a Patient,". For example, if fitting system 206 generates an overloaded generation at block 416, fitting system 206 may randomly select at block 418 a particular number (e.g., 8) of MAPs from this pool of child MAPs. Then, fitting system 206 may use these 8 randomly selected MAPs as the MAPs for the next generation of MAPs for which audible signals presented to the patient 202 at block 406 will be processed.

Fitting system 206 may then return to block 406 and present audible signals processed by this next generation of MAPs to the patient. The process may then continue until either the confidence threshold is exceeded at block 410 or the maximum number of generations is reached at block 414.

Once the confidence threshold or maximum number of generations has been reached, fitting system 206 may then determine, at block 412, the particular MAP to be used by the cochlear implant 100. Various techniques may be used for determining the final MAP depending, for example, on how the process was terminated. For example, if the confidence threshold was reached by a determination that each bit of the MAP is known with a confidence level exceeding the specified confidence level (e.g., 95%), then fitting system 206 may simply use these known bit values for the final MAP. The term final MAP is used in this description to refer to the MAP that is determined by the genetic algorithm and subsequently downloaded to the cochlear implant 100 for use after fitting the implant. However, it should be noted that this MAP may be changed after fitting, such as, for example, by the patient 202 re-fitting the cochlear implant 100 at a later time.

If, however, block 406 is reached due to, for example, the maximum number of generations being reached or a determination that the confidence threshold was exceeded by some other mechanism, fitting system 206 may use various other mechanisms for determining the final MAP. For example, fitting system 206 may present audible signals processed by each of the final selected MAPs to the patient 202 and receive an indication from the patient regarding which MAP is considered the best MAP. Or, for example, fitting system 206 during the process may store an indication regarding each MAP that is selected at block 408 through each iteration, then fitting system 206 may select the MAP that was selected by the patient 202 the most number of times at block 408 and use this MAP as the final MAP.

Or, in yet another example, fitting system 206 may select a number (e.g., 4) of MAPs that were selected by the patient 202 at block 408 the most number of times and present audible signals processed by these selected MAPs (referred to as the final round) to the patient 202. In presenting audible signals processed by the final round of MAPs to the patient, fitting system 206 may provide multiple rounds of presentations, where each MAP is presented to the patient 202 in each round using a different sound token. The patient 202 may then select the "best" MAP for each round, and then after a particular number of rounds (e.g., 4 rounds), the MAP that was selected as best the most amount of times is determined to be the final MAP. If after 4 rounds, there is a tie, a series of one or more rounds may be run for the top tied MAPs to determine the final MAP.

After the final MAP is determined at block 412, fitting system may download this determined MAP to cochlear implant 100 for subsequent use at block 414. In addition, fitting system 206 may store this final MAP along with information identifying the patient 202 and/or cochlear implant 100 in a storage of fitting system 206. Thus, in the event the patient's cochlear implant 100 becomes corrupted, fitting system 100 may be able to more quickly re-provide the determined MAP to cochlear implant. Or, for example, if the genetic algorithm search is repeated for the patient at a later date, an audiologist may be able to view and compare the newly determined MAPs as well as previously determined MAPs for the patient, or even use the previously determined MAP(s) as one of the MAP in the initial generation of the genetic algorithm search.

Figure 6:
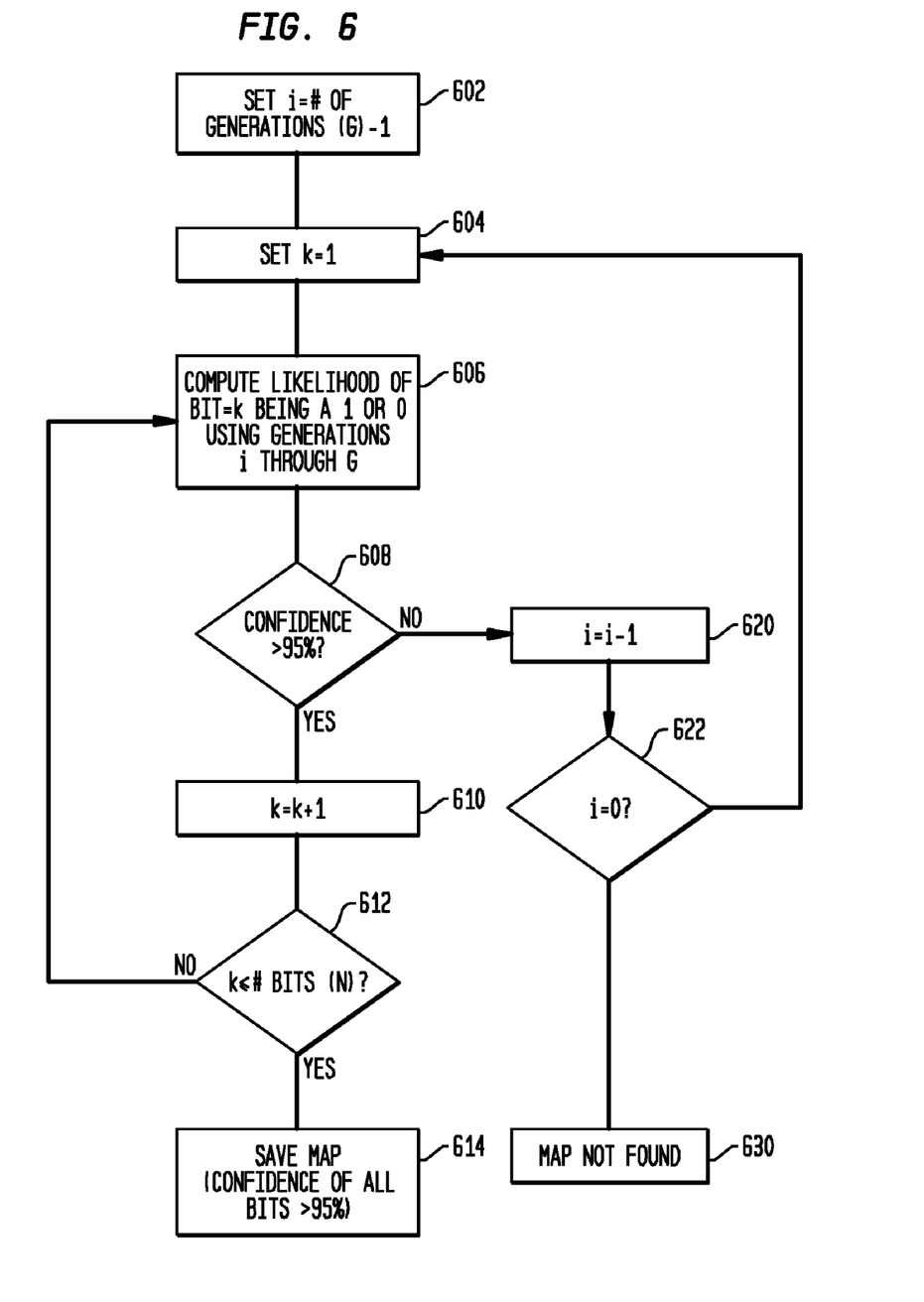
FIG. 6 is a high-level flow chart illustrating operations that may be performed for determining whether the search has converged to an optimal or near-optimal MAP, in accordance with an embodiment.

FIG. 6 is a high-level flow chart illustrating operations that may be performed for determining whether the confidence threshold of the search has been reached, in accordance with an embodiment. FIG. 6 will be discussed with reference to decision 410 of FIG. 4 and the fitting system illustrated in FIG. 2. Further, in this exemplary method, the MAPs are represented by bit maps. This exemplary expedited convergence method allows for the fitting system 206 to exclude early generations in determining whether the bits have converged on a final value.

Initially, fitting system 206 may set at block 602 a counter variable, i, to be equal to one less than the current generation number, G, (i.e., i=G−1). Fitting system 206 may also set a bit counter variable, k, as equal to 1 (k=1) at block 404. Fitting system 206 may then at block 606 compute the likelihood that the kth bit of the MAP is a 1 or a 0 using generations i through the current generation, G. The likelihood that the value of a bit is known is referred to herein as a likelihood of convergence.

In an embodiment, fitting system 206 may compute the likelihood that the kth bit is a 1 or 0 by counting the number of times the kth bit is a 1 in each MAP in generations i through G. For example, in an embodiment, fitting system 206 may store each MAP selected at block 408 along with the generation number when the MAP was selected. Then, fitting system 206 may retrieve all the stored MAPs with a generation number greater than or equal to i, and count the number of times the kth bit of the retrieved MAPs is a 1 and the number of times the kth bit is a 0. Fitting system 206 may then divide each count by the number of MAPs counted in generations i through G to provide the probability that the kth bit is a 1 or a 0. That is, the likelihood the kth bit is a 1 is computed by dividing the number of times the kth bit is equal to a 1 in generations i though G by the number of MAPs in generations i though G. And, the likelihood the kth bit is a 0 is computed by dividing the number of times the kth bit is equal to a 0 in generations i though G by the number of MAPs in generations i though G. It should be noted that this is but one example of a mechanism for computing the likelihood that the kth bit is a 1 or a 0 and other mechanisms may be used. For example, in computing the likelihood, fitting system 206 may use all child MAPs generated at block 418 or, all child MAPs selected at block 420 in computing the likelihood that the kth bit is a 1 or a 0.

After computing the likelihood that the kth bit is a 1 or a 0, fitting system 206 may determine whether either likelihood is greater than a particular confidence level at decision 608. This confidence level may be set to any desired value, and in an embodiment, a bit is considered converged when it is known with a confidence level greater than or equal to 95%. However, in other embodiments, other confidence levels may be used (e.g., 90%, 99%, etc.).

If the computed likelihood of the kth bit being a particular value exceeds the confidence level, the bit variable, k, is increased by 1 at block 612. Then, fitting system 206 may determine at decision 612, whether there are additional bits to be checked. That is, fitting system 206 may check to see if k is less than or equal to the number of bits, N, in each MAP.

If there are additional bits to check, fitting system 206 returns to block 606 and determines if the value of this kth bit is known with a likelihood exceeding the specified confidence level. The process then continues repeats blocks 606 to 612 for each of the N bits of the MAP.

If the value of each bit is known with a likelihood exceeding the specified confidence level (e.g., 95%), the MAP is then saved and the process is considered to have converged on the optimum MAP. Thus, referring back to FIG. 4, the fitting system 206 may consider that confidence threshold has been exceeded at block 410. In other words, in an embodiment, fitting system 206 may determine that the confidence threshold has been met if the likelihood of convergence for each bit in the MAP exceeds the confidence level (e.g., 95%).

Referring back to decision 608, if fitting system 206 determines that any bit is not known with a likelihood exceeding the confidence level, the process may proceed to block 620 and the value of i reduced by 1 (i=i−1). This has the effect of increasing the number of generations (i.e., generations i through G) that will be used in block 606 for computing the likelihood that each bit is a 1 or a 0.

Next, fitting system 206 may check at decision 622 whether the value of i is less than a threshold level. In an embodiment, this threshold level may be set to 0, indicating that the last computation of the likelihood that each bit is known with a particular confidence will be completed using the MAPs for all generations (i.e., including the initial generation of MAPs up through the current generation of MAPs). However, in other embodiments, other threshold levels may be used, such as for example, a threshold level, T, equal to a percentage of G (e.g., T=‖G/2‖)).

If fitting system 206 determines that i remains above the threshold level, T, the process may return to block 604 and fitting system 206 may then determine using generations, i through G, whether the likelihood of each bit of the MAPs is known with the specified confidence level.

If however, fitting system 206 determines that i is less than or equal to the threshold level, T, the process is terminated at block 630. Referring back to decision 410 of FIG. 4, fitting system 206 may then determine that the confidence threshold has not yet been reached and the genetic algorithm search should be continued.

Although the exemplary expedite convergence algorithm of FIG. 6 was discussed above with reference to bit string representations of the MAPs, in other embodiments the method of FIG. 6 may be adapted for MAPs using by data structures in which the actual parameter values are stored. In such an example, the fitting system 206 may determine that a particular parameter has converged if the likelihood that the parameter has any particular value exceeds a particular confidence level (e.g., 95%). Further, as with the embodiment of FIG. 6, early generations may be excluded in computing this likelihood. A further description of MAPs using data structures in which the actual parameter values are stored is provided in the above-referenced U.S. patent application Ser. No. 12/557,208, entitled "Using a Genetic Algorithm to Fit a Medical Implant System to a Patient,".

Referring back to block 408 of FIG. 4, fitting system 206 may use various mechanisms for parent selection. For example, as discussed above, at block 406, the patient 202 may sequentially listen to a sound token processed by each of the MAPs, where the fitting system plays a unique sound token for each provided MAP. Then, the patient 202 may determine which of the audible signals and corresponding MAPs sounded the clearest. For example, in an embodiment, fitting system 202 may provide the patient with 8 MAPs at block 406 and the patient may then select the 4 MAPs that sounded the best to the patient. Or, in another embodiment, the patient 202 need not select a particular number of MAPs that sounded the clearest, but instead, may simply identify the provided MAPs that the patient considered good. A further discussion of exemplary mechanisms for a patient 202 to select a variable number of MAPs is provided in the above-referenced U.S. patent application Ser. No. 12/557,208, entitled "Using a Genetic Algorithm to Fit a Medical Implant System to a Patient,".

In yet another embodiment, rather than the fitting system 206 asking the patient 202 whether the sound perception was good or not, the fitting system 206 may ask the patient 202 what they heard. And, then fitting system 206 may identify the corresponding MAP as good if the patient 202 correctly identifies the sound token. For example, in an embodiment, the sound tokens may comprise spoken phrases. Then, fitting system 206 may present a graphical user interface (GUI) to the patient 202 via display 222 that lets the patient 202 select a graphical list of possible phrases. If the patient 202 selects the correct phrase, the corresponding MAP may be deemed good, while if the incorrect phrase was selected, the corresponding MAP may be deemed bad. That is, if the correct phrase is identified, fitting system 206 may select the corresponding MAP at block 408. While, if the correct phrase is not identified, fitting system 206 may not select the corresponding MAP at block 408. In the event more than the number of desired MAPs (e.g., 4) is identified as good by the patient 202, fitting system 206 may cull the MAPs to reduce the number of selected MAPs as good. And, if less than the number of desired number of MAPs (e.g., 4) is selected, fitting system 206 may randomly select new MAPs from the population of MAPs to act as new parents. It should be noted that these are but some examples of mechanisms that may be used to obtain the desired number of MAPs at block 408 and other mechanisms may be used.

Figure 7:
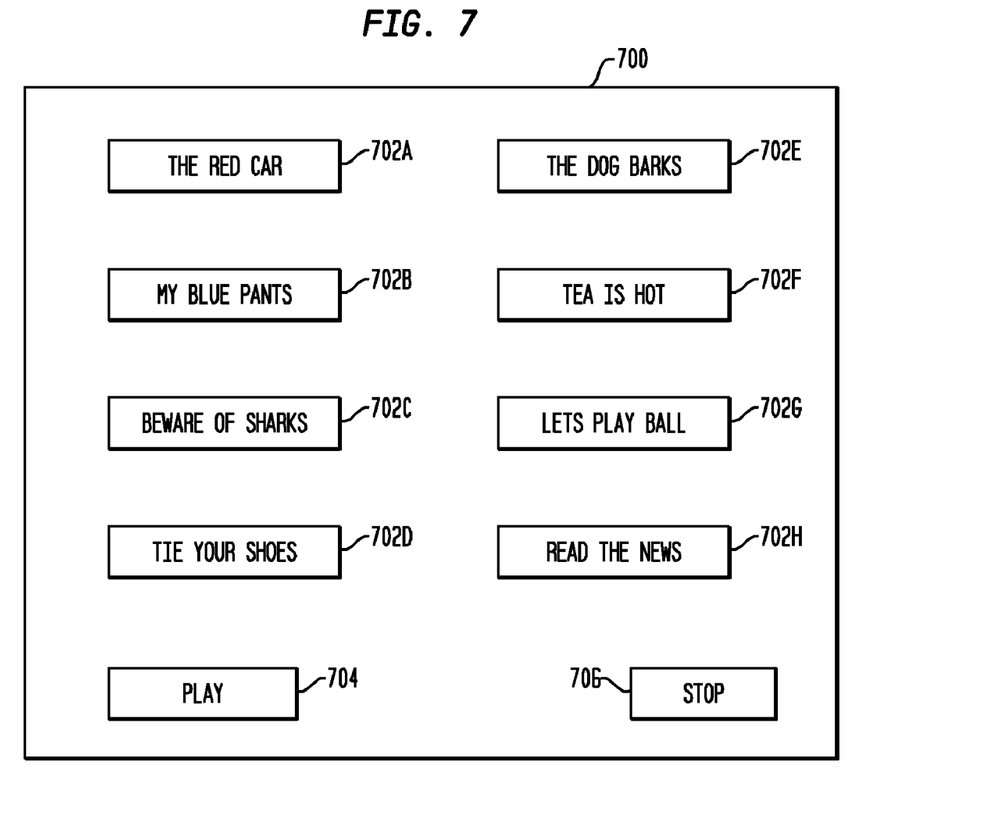
FIG. 7 illustrates an exemplary GUI that may be provided to a recipient for obtaining the recipients perception of applied stimulation, in accordance with an embodiment.

FIG. 7 illustrates an exemplary GUI 700 that may be provided to a recipient for obtaining the recipients perception of applied stimulation, in accordance with an embodiment. As illustrated, GUI 700 may comprise a set of icons 702 that the recipient may select to indicate which phrase they believe they heard. For example, these icons 702 may include an icon for selecting that the recipient heard any one of eight phrases 702A-H. This GUI 700 may be displayed on display 222. The recipient may, using input interface 224, select the icon 702 corresponding to the phrase they believe they heard. The input interface 224 may then provide this response to fitting system controller 212.

Additionally, GUI 700 may include a play icon 704 that the recipient may select to direct the fitting system controller 212 to play the phrase that the patient 202 is to identify. The GUI 700 may also comprise a stop button 706 that the patient 202 may select to stop the process, such as if the recipient needs to leave for any purpose.

It should be noted that GUI 700 is exemplary only and provided to illustrate one example of a GUI interface that may be used for determining whether a patient can correctly identify a sound token processed by a particular MAP. For example, in other embodiments, the sound token may be a sound from a musical instrument and the icons that the recipient may select may be in the shape of different instruments and/or be identified by the name of a particular instrument. Further, in other embodiments, the patient 202 may be able to use check boxes, pull-downs, or other mechanisms for identifying a particular sound.

In an embodiment in which the patient 202 is asked to correctly identify a particular sound, the fitting system 206 may sequentially present audible signals processed by a predetermined number of MAPs (e.g., 8) to the patient each processing a different sound token. Then, the MAPs corresponding to sounds that the patient correctly identified are deemed by the fitting system 206 as good and accordingly selected at block 408. As such, in this example, the number of MAPs selected at block 408 may vary between 0 and all of the presented MAPs (i.e., MAPs used to process audible signals presented to the patient at block 406). In the event no MAPs are selected at block 408, the process may return to block 406 and the previously set of MAPs may be re-presented to the patient 202, although this time with a new set of sound tokens. If, however, no MAPs are again selected at block 408, the process may be re-started and returned to block 404.

In yet another embodiment, the steps of blocks 406 and 408 may be repeated until the patient correctly identifies a particular number of sound tokens (e.g., 4). Then, fitting system 206 may select as parents the MAPs corresponding to the correctly identified sound tokens. For example, in an embodiment, fitting system 418 may randomly select a child MAP from the child MAPs generated at block 418 and then present a sound token processed by the selected MAP to the patient 202. The fitting system 202 may then ask the patient 202 to correctly identify a sound token processed using the MAP. After which, fitting system 206 may randomly select another child MAP and present a sound token processed by this MAP to the patient. This process may then continue until the patient correctly identifies a particular number of sound tokens (e.g., 4). The fitting system 206 may then use the MAPs corresponding to the correctly identified sound tokens as the parent MAPs selected at block 408.

In certain embodiments, certain sound tokens may work better with other MAPs or certain sound tokens may be simply difficult for the patient to understand regardless of the MAP used to process the sound token. For example, if a sound token comprises speech from a person with a strong southern accent, but the patient 202 speaks with a strong English accent, the sound token may be difficult for the patient to identify regardless of the MAP. Thus, it is possible that good MAPs may not be selected at block 408 if they are paired with a bad sound token. In order to mitigate the impact of bad sound tokens, in an embodiment, blocks 406 and 408 may be repeated two or more times. For example, in a first pass through blocks 406 and 408, each MAP may be paired with a particular sound token. Then, during the second pass, the same MAPs and sound tokens may be used, but with different sound tokens matched up with different MAPs. For example, in an embodiment, in the second pass, the MAPs considered bad in the first pass may switch sound tokens with the MAPs considered good in the first pass. As an illustrative example, in a first pass MAP "A" processes token "1," "B" processes token "2," "C" processes token "3", "D" processes token "4", "E" processes token "5," "F" processes token "6," "G" processes token "7," and "H," processes token "8." The, if MAPs A, B, C, and D are selected, in the next pass through blocks 406 and 408 MAP A may be paired with token 5, B with token 6, C with token 7, D with token 8, E with token 1, F with token 2, G with token 3, and H with token 4. Then, at block 408, in the second pass through, fitting system 206 may identify any MAP selected in either pass as good and use these MAPs as parents for generating the next generation.

In yet another embodiment, the genetic algorithm may use two or more populations, rather than a single larger population. For example, the genetic algorithm process may be performed two or more times with a different set of MAP parameters for each genetic algorithm search. In one such example, in the first genetic algorithm search, the parameters represented by the MAP may be more critical parameters. Then in the second genetic algorithm search, the parameters determined in the first search will be fixed and the second genetic algorithm search used to identify less critical parameters. For example, in an embodiment, a first genetic algorithm search may be performed using MAPs that specify the stimulation rate, number of electrodes, and number of Maxima to be used. Other parameters may be set to default values during this first search. Then, the parameter values determined during this first genetic algorithm search are fixed, and the second genetic algorithm search may be performed using these previously determined values as fixed terms. The MAP parameters used in the second genetic algorithm may include parameters, such as values for the type of and shape of filters, etc. In other words, the fitting system 206 may sequentially perform multiple genetic algorithm searches where values for different subsets of parameters are identified in each search, and the values identified in previously performed searches are used as fixed values in subsequent genetic algorithm searches.

The above discussed processes, such as FIGS. 4 and 6, and mechanisms may be embodied on software executable by a computer. Additionally, in an embodiment fitting system 206 may be a patient's home computer, personal digital assistant (PDA) or other device on which such software is loaded. Additionally, in such an embodiment, a piece of hardware may be used for allowing the patient's computer to communicate with the patient's cochlear implant for the purposes of, for example, changing the MAP used by the patient's cochlear implant. This hardware may be connected to the patient's computer, PDA, etc. using for example, as USB interface, a firewire interface or any other suitable mechanism. Or, for example, the patient's computer, PDA, etc. may communicate wirelessly with the patient's cochlear implant using Wi-Fi, Bluetooth, or any other suitable wireless interface included in the computer and cochlear implant. Additionally, in embodiments, the patient could perform optimizations at using signals of his or her own choosing (e.g., a spouse's voice, a musical piece, etc.) or simply using the microphone input of the stimulating medical device. In such embodiment, the software may provide the patient with the ability to upload and store these audible signals for use by the genetic algorithm.

It should be noted that although the above-discussed embodiments were discussed with reference to a cochlear implant, in other embodiments a fitting system may be used to permit a patient 202 to measure the dynamic range of other stimulating medical devices, such as, for example, bone conduction devices, auditory brain stimulators, etc.

Various implementations of the subject matter described, such as the embodiment of FIG. 2, components of may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for at least partially fitting a medical implant system to a patient comprising:
   executing a genetic algorithm to select a determined value set comprising determined values for a plurality of fitting parameters, the genetic algorithm comprising:
      presenting signals processed by a plurality of value sets to the patient using the medical implant system;
      receiving patient feedback in response to the presented signals processed by the value sets;
      selecting, based on the patient feedback, one or more of the value sets;
      computing a likelihood of convergence for at least one determined value of the value set using determined values from a plurality of previously generated generations and not using determined values from one or more of the previously generated generations, the likelihood of convergence for each determined value being a probability that the determined value equals a corresponding reference value;
      generating a successive generation of value sets using said selected one or more value sets; and
      repeating the steps of presenting, receiving, selecting, and generating until the computed likelihood of convergence exceeds a confidence level; and
   providing said determined value set to said medical implant system for use in providing stimulation to the patient.

2. The method of claim 1, wherein computing a likelihood of convergence for at least one determined value of the value set comprises:
   computing a likelihood of convergence for each determined value of the value set; and
   wherein repeating the steps until the likelihood of convergence exceeds the confidence level comprises:
   repeating the steps until the likelihood of convergence for each determined value exceeds the confidence level.

3. The method of claim 1, wherein computing a likelihood of convergence for at least one value comprises:
   computing a first likelihood of convergence for the at least one determined value using determined values from a first set of previously generated generations; and
   computing a second likelihood of convergence for the at least one determined value using values from a second set of previously generated generations; and
   wherein repeating the steps of presenting, receiving, selecting, and generating until the computed likelihood of convergence exceeds a confidence level comprises:
   repeating until either the first or second computed likelihood of convergence exceeds the confidence level.

4. The method of claim 1, wherein each determined value of the value set is represented by at least one bit; and wherein computing a likelihood of convergence for each determined value comprises:
   computing a likelihood of convergence for each bit.

5. The method of claim 1, wherein presenting signals processed by a plurality of value sets comprises:
   providing a value set to the medical implant system; and
   providing a signal to the patient that is processed by the medical implant system using the provided value set.

6. The method of claim 5, wherein presenting signals processed by a plurality of value sets comprises:
   providing a graphical user interface to the patient that comprises one or more icons corresponding to a possible identification of the signal; and
   wherein receiving patient feedback comprises:
   receiving an indication regarding a particular icon selected by the patient; and
   wherein selecting one or more of the value sets comprises:
   selecting the value set if the selected icon correctly identifies the signal.

7. The method of claim 5, wherein providing a plurality of value sets comprises:
   providing a value set to the medical implant system;
   providing a first signal to the patient system that is processed by the medical implant system using the provided value set; and
   providing a second signal to the patient system that is processed by the medical implant system using the provided value set; and
   wherein receiving patient feedback comprises:
   receiving patient feedback regarding the provided first signal processed using the provided value set; and receiving patient feedback regarding the provided second signal processed using the provided value set.

8. The method of claim 1 wherein executing the genetic algorithm comprises:
   executing a first genetic algorithm to select a first determined value set comprising values for a plurality of fitting parameters; and
   executing a second genetic algorithm to select a second determined value set comprising values for a plurality of fitting parameters, wherein the first value set is used in executing the second genetic algorithm.

9. The method of claim 1, wherein the medical implant system is a cochlear implant system and wherein the signals are audible signals.

10. A system for at least partially fitting a medical implant system to a patient comprising:
   a processor configured to execute a genetic algorithm to select a determined value set comprising determined values for a plurality of fitting parameters, wherein the processor in executing the genetic algorithm is configured to:
      present a plurality of value sets to the patient using the medical implant system,
      receive patient feedback in response to the presented signals processed by the value sets, select, based on the patient feedback, one or more of the value sets,
      compute a likelihood of convergence for at least one determined value of the value set using values from a plurality of previously generated generations and not using determined values from one or more of the previously generated generations, the likelihood of convergence for each determined value being a probability that the determined value equals a corresponding reference value,
      generate a successive generation of value sets using said selected one or more value sets; and
      repeat the steps of presenting, receiving, selecting, and generating until the computed likelihood of convergence exceeds a confidence level; and
   an interface configured to provide at least one of the value sets to the medical implant system for use by the medical implant system in providing stimulation to the patient.

11. The system of claim 10, wherein the processor in computing a likelihood of convergence for at least one determined value of the value set is configured to compute a likelihood of convergence for each determined value of the value set; and wherein the processor in repeating the steps until the likelihood of convergence exceeds the confidence level is configured to repeat the steps until the likelihood of convergence for each determined value exceeds the confidence level.

12. The system of claim 10, wherein the processor in computing a likelihood of convergence for at least one determined value is configured to compute a first likelihood of convergence for the at least one determined value using values from a first set of previously generated generations, and compute a second likelihood of convergence for the at least one determined value using values from a second set of previously generated generations; and wherein the processor in repeating the steps of presenting, receiving, selecting, and generating until the computed likelihood of convergence exceeds a confidence level is configured to repeat the steps until either the first or second computed likelihood of convergence exceeds the confidence level.

13. The system of claim 10, wherein each determined value of the value set is represented by at least one bit; and wherein the processor in computing a likelihood of convergence for each determined value is configured to compute a likelihood of convergence for each bit.

14. The system of claim 10, wherein the processor in presenting signals processed by a plurality of value sets is configured to provide a value set to the medical implant system, and provide a signal to the patient that is processed by the medical implant system using the provided value set.

15. The system of claim 14, wherein the processor in presenting signals processed by a plurality of value sets is configured to provide a graphical user interface to the patient that comprises one or more icons corresponding to a possible identification of the signal; and wherein the processor in receiving patient feedback is configured to receive an indication regarding a particular icon selected by the patient; and wherein the processor in selecting one or more of the value sets is configured to select the value set if the selected icon correctly identifies the signal.

16. The system of claim 15, wherein the processor in providing a plurality of value sets is configured to provide a value set to the medical implant system, provide a first signal to the patient system that is processed by the medical implant system using the provided value set, and provide a second signal to the patient system that is processed by the medical implant system using the provided value set; and
   wherein the processor in receiving patient feedback is configured to receive patient feedback regarding the provided first signal processed using the provided value set, and receive patient feedback regarding the provided second signal processed using the provided value set.

17. The system of claim 10 wherein the processor in executing the genetic algorithm is configured to execute a first genetic algorithm to select a first determined value set comprising values for a plurality of fitting parameters, and execute a second genetic algorithm to select a second determined value set comprising values for a plurality of fitting parameters, wherein the first value set is used in executing the second genetic algorithm.

18. The system of claim 10, wherein the medical implant system is a cochlear implant system and wherein the signals are audible signals.

19. A system for at least partially fitting a medical implant system to a patient comprising:
   means for executing a genetic algorithm to select a determined value set comprising determined values for a plurality of fitting parameters, the genetic algorithm comprising:
      means for presenting signals processed by a plurality of value sets to the patient using the medical implant system;
      means for receiving patient feedback in response to the presented signals processed by the value sets;
      means for selecting, based on the patient feedback, one or more of the value sets;
      means for computing a likelihood of convergence for at least one determined value of the value set using determined values from a plurality of previously generated generations and not using determined values from one or more of the previously generated generations, the likelihood of convergence for each determined value being a probability that the determined value equals a corresponding reference value;
      means for generating a successive generation of value sets using said selected one or more value sets; and
      means for repeating the steps of presenting, receiving, selecting, and generating until the computed likelihood of convergence exceeds a confidence level; and means for providing said determined value set to said medical implant system for use in providing stimulation to the patient.

20. A non-transitory computer-readable media encoded with instructions operative to cause a computer to perform a method for at least partially fitting a medical implant system to a patient, the method comprising:
  executing a genetic algorithm to select a determined value set comprising determined values for a plurality of fitting parameters, the genetic algorithm comprising:
    presenting signals processed by a plurality of value sets to the patient using the medical implant system;
    receiving patient feedback in response to the presented signals processed by the value sets;
    selecting, based on the patient feedback, one or more of the value sets;
    computing a likelihood of convergence for at least one determined value of the value set using determined values from a plurality of previously generated generations and not using determined values from one or more of the previously generated generations, the likelihood of convergence for each determined value being a probability that the determined value equals a corresponding reference value;
    generating a successive generation of value sets using said selected one or more value sets; and
    repeating the steps of presenting, receiving, selecting, and generating until the computed likelihood of convergence exceeds a confidence level; and
  providing said determined value set to said medical implant system for use in providing stimulation to the patient.

21. The method of claim 1, wherein, in the genetic algorithm, the computing a likelihood of convergence includes:
  making a first count of the number of previously generated generations in the plurality thereof;
  making a second count, for each determined value, the number of instances in which the determined value was equal to the corresponding reference value; and
  dividing the second count by the first count thereby to obtain the probability.

22. The system of claim 10, wherein the processor in computing a likelihood of convergence for at least one determined value of the value set is configured to:
  make a first count of the number of previously generated generations in the plurality thereof;
  make a second count, for each determined value, the number of instances in which the determined value was equal to the corresponding reference value; and
  divide the second count by the first count thereby to obtain the probability.

23. The system of claim 19, wherein the means for computing a likelihood of convergence is further configured to:
  make a first count of the number of previously generated generations in the plurality thereof;
  make a second count, for each determined value, the number of instances in which the determined value was equal to the corresponding reference value; and
  divide the second count by the first count thereby to obtain the probability.

24. The computer-readable media of claim 20, wherein, in the genetic algorithm, the computing a likelihood of convergence includes:
  making a first count of the number of previously generated generations in the plurality thereof;
  making a second count, for each determined value, the number of instances in which the determined value was equal to the corresponding reference value; and
  dividing the second count by the first count thereby to obtain the probability.

* * * * *